United States Patent [19]

Ohno et al.

[11] Patent Number: 4,713,457

[45] Date of Patent: Dec. 15, 1987

[54] ERGOLINE DERIVATIVES AND ACID ADDITION SALTS THEREOF

[75] Inventors: Sachio Ohno; Yuko Ebihara; Kiyoshi Mizukoshi, all of Aichi; Kenji Ichihara, Gifu; Takao Ban; Mitsuaki Nagasaka, both of Aichi, all of Japan

[73] Assignee: Maruko Seiyaku Co., Ltd., Nagoya, Japan

[21] Appl. No.: 831,676

[22] Filed: Feb. 21, 1986

[30] Foreign Application Priority Data

Feb. 21, 1985 [JP] Japan .................................. 60-33430
Dec. 28, 1985 [JP] Japan ................................ 60-299203

[51] Int. Cl.$^4$ ..................... A61K 31/48; C07D 457/00
[52] U.S. Cl. ...................................... 546/67; 514/288
[58] Field of Search ........................... 546/67, 68, 69; 514/288

[56] References Cited

U.S. PATENT DOCUMENTS 4,199,579  4/1980  Ferrari et al. ......................... 424/246
4,321,381  3/1982  Mantegani et al. ................... 546/67

FOREIGN PATENT DOCUMENTS 896609    8/1983  Belgium .
171570   11/1978  Czechoslovakia .
1115      3/1979  European Pat. Off. .
8802      3/1980  European Pat. Off. .
56358     7/1982  European Pat. Off. .
126968    5/1984  European Pat. Off. .............. 546/68
0128479  12/1984  European Pat. Off. .
2617738  11/1976  Fed. Rep. of Germany .
2802023   8/1978  Fed. Rep. of Germany .
2810774  10/1978  Fed. Rep. of Germany .
2935685   3/1980  Fed. Rep. of Germany .
2935684   3/1980  Fed. Rep. of Germany .
3026271   2/1981  Fed. Rep. of Germany .
3240727   5/1983  Fed. Rep. of Germany .
2421176  10/1979  France .
2434814   3/1980  France .
2479829  10/1981  France .
53-84996  7/1978  Japan .
54-115400 9/1979  Japan .
55-89282  7/1980  Japan .
56-156279 12/1981 Japan .
57-156485 9/1982  Japan .
58-85886  5/1983  Japan .
58-194884 11/1983 Japan .
59-176285 10/1984 Japan .
59-206382 11/1984 Japan .
60-84286  5/1985  Japan .
508102   10/1982  Spain .
551975    7/1974  Switzerland .
551976    7/1974  Switzerland .
2056437   3/1981  United Kingdom ................. 546/67
2120242   4/1983  United Kingdom .

OTHER PUBLICATIONS

Bernardi et al, "Antihypertensive Ergolinepropionamides", Arzneim.-Forsch., vol. 33 (1983), pp. 1094–1098.
"10-Methoxyergoline Derivatives as a-Adrenergic Blocking Agents", Experimentia, vol. 28, pp. 819–823.
Salvati et al, "Cardiovascular Effects of a New Antihypertensive Agent in Several Species", Arzneim.-Forsch., vol. 33 (1983), pp. 1098–1107.
Hollenberg, "The Kidney and Strategies for the Treatment of Hypertension", vol. 77(4a), (10/5/84), pp. 60–63.
Weinstock et al, "Synthesis and Renal Vasodilator . . . Fenoldopam", vol. 29 (1986), pp. 2315–2325.
Jap. J. Pharmacol., 40 (Suppl.) (1986), p. 174.
Folia Pharmacol., Japan, vol. 87 (1986), pp. 445–456.
Seiler et al, "Structure-Activity Relationship of . . . Substituents", J. Med. Chem., vol. 29 (1986), pp. 912–917.
Stumpe et al, "Hyperprolactinaemia and . . . Hypertension", The Lancet, Jul. 30, 1977, pp. 211–214.
Lievre et al, "Einfluss auf die zerebrale . . . Nicergolin", Arzneim.-Forsch., vol. 29 (1979), pp. 1227–1231.
Cassady et al, "Ergot Alkaloids . . . Release", J. Med. Chem., vol. 17, No. 3, (1974), pp. 300–307.
Stutz et al, "Ergot Alkaloids. New Ergolines . . . Stimulants", J. Med. Chem., vol. 21, No. 8, (1978), pp. 754–757.
Sanka to Fujinka, vol. 48 (1981), pp. 117–123, 241.
Yakuri to Chiryo, vol. 12, No. 1 (1/84), pp. 401–407.
Crider et al, "Convenient Synthesis . . . Ester", Journal of Pharmaceutical Science, vol. 70, No. 12 (12/81), pp. 1319–1321.
Benez et al, "2-Acylated Derivatives of Ergoline", Collection Czechoslovak Chem. Commun., vol. 47 (1982), pp. 1757–1761.
Beran et al, Collection, Czechoslov. Chem. Commun., vol. 42 (1977), pp. 1407–1411.
Beran et al, "Some O-Acyl Derivatives . . . Ergoline(I)", Collection Czechoslov. Chem. Commun., vol. 39 (1974), pp. 1768–1772.
Calne et al, "Bromocriptine in Parkinsonism", British Med. Journal, vol. 4 (1974), pp. 442–444.
Fluckiger et al, "Two Novel Prolactin Release-Inhibiting . . . ", Experientia, vol. 35 (1979), pp. 1677–1678.

(List continued on next page.)

Primary Examiner—Donald G. Daus
Assistant Examiner—Cecilia Shen
Attorney, Agent, or Firm—Sughrue, Mion, Zinn, Macpeak, and Seas

[57] ABSTRACT

Novel ergoline derivatives and acid addition salts thereof are disclosed. These ergoline derivatives possess excellent anti-hypertensive activity, vasodilating activity, anti-ulcer activity, gastric secretion inhibitory activity, brain metabolism improving activity, anti-depressive activity and dopamine-like activity, and, therefore, are useful for prevention and treatment of various diseases such as hypertension, a wide variety of vein disorders, peptic ulcer, brain absormality, depression, Parkinson's disease, high prolactin blood disease, etc.

3 Claims, No Drawings

OTHER PUBLICATIONS

Crider et al, Ergot Alkaloids, J. Med. Chem. 1977, vol. 20, No. 11, pp. 1473–1477.

Sved et al, "Evidence for a Peripheral . . . Lergotrile", Life Sciences, vol. 27, (1981), pp. 349–354.

Cavero et al, "Pergolide Decreases Arterial . . . Dogs", Br. J. Pharmacol., vol. 75 (1982), pp. 142–143.

Moretti, "Metabolische und . . . Zentralnervensystem", Arzneim.-Forsch., vol. 29 (1979), pp. 1213–1223.

Enz, "Biphasic Influence . . . Rat", Life Sciences, vol. 29 (1981), pp. 2227–2234.

Snider, "Correlation of Behavioural Inhibition . . . Turnover", J. Pharm Pharmacol. (1976), pp. 563–566.

Li et al, "Ergot Akaloids . . . Release", Journal of Medicinal Chemistry, vol. 18, No. 9 (1975), pp. 892–895.

Manske, "The Alkaloids", vol. XV (1975), pp. 1–40.

ERGOLINE DERIVATIVES AND ACID ADDITION SALTS THEREOF

FIELD OF THE INVENTION

This invention relates to novel ergoline derivatives and the acid addition salts thereof which are useful as pharmaceutical agent. More particularly, the present invention relates to novel ergoline derivatives represented by the formula (I) below having excellent anti-hypertensive activity, vasodilating activity, anti-ulcer activity, gastric secretion inhibitory activity, brain metabolism improving activity, anti-depressive activity and dopamine-like activity and, therefore, are useful for prevention and treatment of various diseases such as hypertension, a wide variety of vein disorders, peptic ulcer, brain abnormality, depression, Parkinson's disease, high prolactin blood disease, etc.

BACKGROUND OF THE INVENTION

Hitherto, ergotamine and ergometrine which are ergot-alkaloids have been used as pharmaceutical agents for treatment of migrain and as an uterine contracting agent, respectively. Also, various semi-synthesized alkaloids have been used clinically, and typical examples of such alkaloids include methylergometrine (as uterine contracting agent), dihydroergotamine (as agents for treatment of orthostatic hypotensive asthenia and migrain), dihydroergotoxine (as agent for improving brain and peripheral circulation disorders and as anti-hypertensive agent), bromocryptin (as agent for treatment of acromegalia, pituitary giantism and Parkinson's disease).

These ergot-alkaloids and compounds related thereto possess various pharmacological activities, and have been known to have hypotensive, vasodilating, anti-ulcer, gastric secretion inhibitory, brain metabolism improving activity, anti-depressive activities as well as dopamine-like activity as described in, for example, *The Alkaloids*, Vol. 15, Academic Press, 1975, pp1–40 and literature references cited therein; *Life Science*, 27, 349 (1980); *Br. J. Pharmacol.*, 75, 143p (1982); *Arzneim.-Forsch.*, 29, 1227 (1979); ibid., 29, 1213 (1979); German Offen., No. 2,617,738; *J. Med. Chem.*, 21, 754 (1978); *Life Science*, 29, 2227 (1981); *J. Pharm. Pharmacol.*, 28, 563 (1976); *J. Med. Chem.*, 17, 300 (1974); ibid, 18, 892 (1975); ibid, 20, 1473 (1977); *Experientia.*, 35, 1677 (1979); *Br. Med. J.*, 4, 442 (1974), etc.

Further, extensive studies have been conducted on alkaloids for the purpose of developing pharmaceutical agents having excellent pharmacological activities as described in, for example, *Collect. Czech. Chem. Commun.*, 39, 1768 (1974), ibid, 42, 1407 (1977), ibid, 47, 1757 (1982); *J. Pharm. Sci.*, 70, 1319 (1981); *Experientia*, 28, 819 (1972); *Yakuri to Chiryo* (Pharmacology and Treatment), 12, 402 (1984); *Arzneim.-Forsch.*, 33, 1094 (1983), ibid, 33, 1098 (1983); Swiss Pat. Nos. 551,975 and 551,976 (1976); Czech. Pat. No. 171,570 (1978); German Offen., Nos. 2,802,023 and 2,810,774 (1978), 2,935,685 and 2,935,684 (1980), 3,026,271 (1981), 3,240,727 (1983); European Patent Application No. 1,115 (1979), 8,802 (1980), 56,358 (1982); Fr. Demmande Nos. 2,421,176 (1979), 2,434,814 (1980), 2,479,829 (1981); U.S. Pat. Nos. 4,199,579 (1980), 4,321,381 (1982); Belgian Pat. Nos. 870,414 (1979), 896,609 (1983); Spanish Pat. No. 508,102 (1982); Japanese Patent Application (OPI) Nos. 53-84996, 54-115400, 55-89282, 56-156279, 57-156485, 58-194884, 58-85886, 59-176285, etc. (The term "OPI" as used herein refers to an unexamined published Japanese patent application.)

On the other hand, the compounds having an ergolin-8-ylmethyl group bonded to a 5-membered heterocyclic group have been reported in a small number of prior art references, e.g., Japanese Patent Application (OPI) Nos. 58-194884 59-206382 and 60-84286. Further, there is only a very limited number of publications, e.g., Japanese Patent Application (OPI) No. 59-206382 and 60-84286, with respect to the compounds wherein an ergolin-8-ylmethyl group is directly bonded to the nitrogen atom of a 5-membered heterocyclic group containing at least one nitrogen atom, which are closely related to the compounds of this invention.

Although these prior art compounds have excellent pharmacological activities, they are still unsatisfactory because of their weak activity, low selectivity of effects, and/or high toxicity.

As a result of extensive studies on ergot-alkaloid related compounds, the present inventors found that ergoline derivatives of the formula (I) of the present invention and the pharmaceutically acceptable acid addition salts thereof have excellent pharmacological activities.

DETAILED DESCRIPTION OF THE INVENTION

The ergoline derivatives of the present invention are represented by the formula (I)

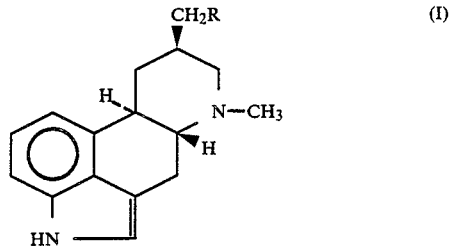

wherein R represents a 5-membered heterocyclic group which contains at least one nitrogen atom as a hetero atom and which is a monovalent group on the nitrogen atom thereof, selected from the group consisting of an imidazol-1-yl group, a 2-oxooxazolidin-3-yl group, a 1,2,4-triazol-1-yl group, a tetrazole group, a succinimido group, a 2-methylimidazol-1-yl group, a 2-ethylimidazol-1-yl group, a 2-isopropylimidazol-1-yl group, a 2-propylimidazol-1-yl group, a 2-phenylimidazol-1-yl group, a 2-ethyl-4-methylimidazol-1-yl group, a 5-ethoxycarbonyl-4-methylimidazol-1-yl group and a 4-ethoxycarbonyl-5-methylimidazol-1-yl group, and acid addition salts thereof.

The compounds of the formula (I) of this invention can be prepared easily by reacting a sulfonate represented by the formula (II)

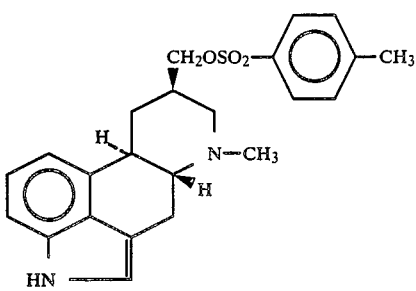
(II)

which is described in *Helv. Chim. Acta.*, 41, 1984 (1958), *Collect. Czech. Chem. Commun.*, 33, 577 (1968), etc., with imidazole, oxazolidin-2-one, 1,2,4-triazole, tetrazole, succinimide, 2-methylimidazole, 2-ethylimidazole, 2-isopropylimidazole, 2-propylimidazole, 2-phenylimidazole, 2-ethyl-4-methylimidazole or ethyl 4-methylimidazole-5-carboxylate, in the presence of a base such as sodium hydride, potassium carbonate, sodium carbonate, etc. Alternatively, the reaction can be effected using a metal salt of the above 5-membered heterocyclic reactant such as sodium salt or potassium salt. In either case, the reaction can be carried out in an inert solvent such as dimethylformamide, dimethyl sulfoxide, hexamethylphosphortriamide, acetone, methyl ethyl ketone, etc. at a temperature of about 30° to about 120° C. for a period of from about 0.5 to about 15 hours, using 1 mole to a large molar excess of the 5-membered heterocyclic reactant or a metal salt thereof per mole of the sulfonate represented by the formula (II), i.e., 6-methylergolin-8β-ylmethyl tosylate.

The compounds of the formula (I) according to the present invention can be converted into pharmaceutically acceptable acid addition salts thereof in a conventional manner. Preferred examples of the acid addition salts include those formed with pharmaceutically acceptable acids such as fumaric acid, maleic acid, tartaric acid, hydrochloric acid, sulfuric acid, methanesulfonic acid and the like.

The compounds of the formula (I) and the acid addition salts thereof exhibit markedly excellent anti-hypertensive activity, vasodilating activity, anti-ulcer activity, gastric secretion inhibitory activity, brain metabolism improving activity, anti-depressive activity and dopamine-like activity as demonstrated in Examples 16 to 21 hereinafter described.

In administering the compounds of this invention, these compounds can be formulated, alone or in combination with other ingredients, into various pharmaceutical preparations such as tablets, troches, pills, granules, powders, capsules, ampules, suppositories and the like. Examples of other ingredients include pharmaceutical diluents, carriers or excipients, lubricating agents, disintegrating agents, etc., for example, starch, dextrin, sucrose, lactose, silicic acid, carboxymethyl cellulose, gelatin, polyvinylpyrrolidone, glycerin, agar, calcium carbonate, sodium bicarbonate, paraffins, cetyl alcohol, stearic acid esters, kaolin, bentonite, talc, calcium stearate, magnesium stearate, polyethylene glycol, water, ethanol, isopropyl alcohol, polypropylene glycol, etc.

The daily dosage of the compounds of the formula (I) and the acid addition salts thereof for oral administration may vary from about 0.05 to about 20 mg per Kg of the body weight. The dosage level can, of course, be varied depending upon the severity of conditions and the particular type of disease to be treated, and so on. These compounds can be administered in a single dose or multiple doses.

The present invention is further illustrated in greater detail by the following Examples, but the present invention is not limited thereto.

EXAMPLE 1

1-(6-Methylergolin-8β-ylmethyl)imidazole 1.0 g of 50% sodium hydride in an oil was added in small portions to a mixture of 2.0 g of imidazole and 20 ml of dimethylformamide, and the resulting mixture was stirred for 30 minutes. 3.0 g of 6-methylergolin-8β-ylmethyl tosylate was added to the mixture which was then heated on a water bath for 3 hours. After allowing the mixture to cool, ice-water was added to the reaction mixture, and the precipitated crystals were filtered and washed with water. The crystals thus obtained were dissolved in ethanol, and the solution was concentrated to a volume of about ⅓, followed by allowing to cool to obtain 1.3 g of the titled compound as colorless prisms having a melting point of higher than 260° C. (with decomposition).

NMR (CD$_3$OD) δ: 1.12 (1H, q, J=11.6 Hz), 1.80–3.05 (7H, m), 2.40 (3H, s), 3.96 (2H, d, J=6.3 Hz), 6.63–7.20 (6H, m), 7.64 (1H, br s).

NMR (DMSO-d$_6$) δ: 1.01 (1H, q, J=11.9 Hz), 1.68–2.94 (7H, m), 3.26 (1H, dd, J=14.2, 5.4 Hz), 3.91 (2H, d, J=6.6 Hz), 6.57–7.23 (6H, m), 7.60 (1H, s), 10.73 (1H, br s).

Elementary Analysis for C$_{19}$H$_{22}$N$_4$: Calc'd: C, 74.48; H, 7.24; N, 18.29. Found: C, 74.58; H, 7.47; N, 18.02.

The fumarate salt of the above compound was colorless needles and had a melting point of 205°–212° C. (with decomposition) after recrystallization from methanol-ethanol.

EXAMPLE 2

3-(6-Methylergolin-8β-ylmethyl)oxazolidin-2-one 0.5 g of 50% sodium hydride in an oil was added in small portions to a mixture of 2.0 g of oxazolidin-2-one and 15 ml of dimethylformamide, and the resulting mixture was stirred for 30 minutes. 2.0 g of 6-methylergolin-8β-ylmethyl tosylate was added to the mixture which was then heated on a water bath for 1 hour. The solvent was distilled off under reduced pressure, and the residue (which was dissolved in dichloromethane and adsorbed on silica gel) was purified by silica gel column chromatography (eluted with ethyl acetate:isopropyl alcohol=1:1 by volume). The product was recrystallized from isopropyl alcohol to obtain 1.3 g of the titled compound as colorless needles having a melting point higher than 240° C. (with decomposition).

NMR (CDCl$_3$) δ: 1.15 (1H, q, J=11.8 Hz), 1.82–3.83 (12H, m), 2.47 (3H, s), 4.20–4.47 (2H, m), 6.75–7.23 (4H, m), 7.98 (1H, br).

IR (KBr) cm$^{-1}$: 1764 (CO).

Elementary Analysis for C$_{19}$H$_{23}$N$_3$O$_2$: Calc'd: C, 70.13; H, 7.12; N, 12.91. Found: C, 70.01; H, 7.34; N, 12.88.

EXAMPLE 3

1-Methyl-3-(6-methylergolin-8β-ylmethyl)imidazolidin-2,4-dione

A mixture of 0.5 g of 6-methylergolin-8β-ylmethyl tosylate, 1.0 g of 1-methylimidazolidin-2,4-dione, 1.0 g of potassium carbonate, 10 ml of methyl ethyl ketone and 10 ml of dimethylformamide was refluxed for 4 hours with stirring, and the solvent was distilled off under reduced pressure. Water was added to the residue, and the mixture was extracted with dichloromethane. The organic layer was washed with water, dried over magnesium sulfate, and the solvent was distilled off. The residue (which was dissolved in dichloromethane and adsorbed on silica gel) was purified by silica gel column chromatography (eluted with ethyl acetate and then with ethyl acetate:isopropyl alcohol=1:1 by volume). The product was recrystallized from dichloromethane-hexane to obtain 0.3 g of the titled product as colorless needles having a melting point higher than 210° (with decomposition).

NMR (CDCl$_3$) δ: 1.18 (1H, q, J=11.8 Hz), 1.86–3.10 (7H, m), 2.45 (3H, s), 3.01 (3H, s), 3.38 (1H, dd, J=14.4, 4.2 Hz), 3.49 (2H, d, J=6.2 Hz), 3.87 2H, s), 6.77–7.26 (4H, m), 7.88 (1H, br).

IR (KBr) cm$^{-1}$: 3410 (NH), 1768 (CO), 1715 (CO).

Elementary Analysis for $C_{20}H_{24}N_4O_2.1/12CH_2Cl_2$: Calc'd: C, 67.10; H, 6.78; N, 15.58. Found: C, 67.21; H, 7.04; N, 15.38.

EXAMPLE 4

1-(6-Methylergolin-8β-ylmethyl)pyrazole 0.7 g of 50% sodium hydride in an oil was added in small portions to a mixture of 2.5 g of pyrazole and 20 ml of dimethylformamide, and the resulting mixture was stirred for 30 minutes. 2.5 g of 6-methylergolin-8β-ylmethyl tosylate was added to the mixture which was then heated on a water bath for 1 hour. The solvent was distilled off under reduced pressure, and water was added to the residue. The precipitated crystals were separated by filtration, washed with water and recrystallized from dichloromethane-isopropyl ether to obtain 1.7 g of the titled compound as colorless flakes having a melting point of 192°–194° C.

NMR (CDCl$_3$) δ: 1.15 (1H, q, J=12.5 Hz), 1.81–3.10 (7H, m), 3.41 (3H, s), 3.35 (1H, dd, J=14.7, 4.4 Hz), 3.85–4.27 (2H, m), 6.24 (1H, t, J=2.3 Hz), 6.69–7.17 (4H, m), 7.35 (1H, d, J=2.3 Hz), 7.48 (1H, d, J=2.1 Hz), 8.13 (1H, br).

Elementary Analysis for $C_{19}H_{22}N_4$: Calc'd: C, 74.48; H, 7.24; N, 18.29. Found: C, 74.56; H, 7.60; N, 18.08.

EXAMPLE 5

3,5-Dimethyl-1-(6-methylergolin-8β-ylmethyl)pyrazole 0.7 g of 50% sodium hydride in an oil was added in small portions to a mixture of 1.9 g of 2,5-dimethylpyrazole and 50 ml of dimethylformamide, and the resulting mixture was stirred for 30 minutes. 2.0 g of 6-methylergolin-8β-ylmethyl tosylate was added to the mixture which was then heated on a water bath for 3 hours. The solvent was distilled off under reduced pressure, and the residue was purified by silica gel column chromatography (eluted with ethyl acetate:ethanol=10:1 by volume). The product was recrystallized from isopropyl alcohol to obtain 0.8 g of the titled compound as colorless prisms having a melting point of 187°–190° C.

NMR (CDCl$_3$) δ: 1.19 (1H, q, J=12.5 Hz), 1.83–3.11 (7H, m), 2.21 (3H, s), 2.25 (3H, s), 2.43 (3H, s), 3.37 (1H, dd, J=14.3, 4.1 Hz), 3.92 (2H, d like), 5.76 (1H, s), 6.74–6.95 (2H, m), 7.84 (1H, br).

EXAMPLE 6

1-(6-Methylergolin-8β-ylmethyl)-1,2,4-triazole 0.4 g of 50% sodium hydride in an oil was added in small portions to a mixture of 2.0 g of 1,2,4-triazole and 20 ml of dimethylformamide, and the resulting mixture was stirred for 30 minutes. 2.0 g of 6-methylergolin-8β-ylmethyl tosylate was added to the mixture which was then heated on a water bath for 1 hour. After allowing the mixture to cool, water was added to the reaction mixture, and the precipitated crystals were separated by filtration, washed with water and purified by alumina column chromatography (eluted with dichloromethane). The product was recrystallized from methanol to obtain 0.8 g of the titled compound as colorless needles having a melting point of 245°–253° C.

NMR (CDCl$_3$) δ: 1.19 (1H, q, J=12.9 Hz), 1.85–3.13 (7H, m), 2.44 (3H, s), 3.37 (1H, dd, J=14.3, 3.8 Hz), 4.14 (2H, d like), 6.71–6.94 (2H, m), 6.97–7.23 (2H, m), 7.90 (1H, br), 7.93 (1H, s), 8.48 (1H, s).

Elementary Analysis for $C_{18}H_{21}N_5$: Calc'd: C, 70.33; H, 6.89; N, 22.73. Found: C, 70.42; H, 7.07; N, 22.73.

EXAMPLE 7

1-(6-Methylergolin-8β-ylmethyl)tetrazole 1.7 g of 50% sodium hydride in an oil was added in small portions to a mixture of 5.1 g of tetrazole and 30 ml of dimethylformamide, and the resulting mixture was stirred for 30 minutes. 3.0 g of 6-methylergolin-8β-ylmethyl tosylate was added to the mixture which was then heated on a water bath for 11 hours. The solvent was distilled off under reduced pressure, and the residue was purified by alumina column chromatography (eluted with acetone). The product was recrystallized from acetone to obtain 0.7 g of the titled compound as colorless needles having a melting point of 206°–209° C.

NMR (CDCl$_3$) δ: 1.26 (1H, q, J=12.5 Hz), 1.82–3.13 (7H, m), 2.42 (3H, s), 3.37 (1H, dd, J=14.3, 3.9 Hz), 4.60 (2H, d, J=6.3 Hz), 6.68–6.92 (2H, m), 6.97–7.20 (2H, m), 7.89 (1H, br), 8.46 (1H, s).

Elementary Analysis for $C_{17}H_{20}N_6$: Calc'd: C, 66.21; H, 6.54; N, 27.25. Found: C, 66.46; H, 6.53; N, 27.65.

EXAMPLE 8

N-(6-methylergolin-8β-ylmethyl)succinimide 0.8 g of 50% sodium hydride in an oil was added in small portions to a mixture of 3.4 g of succinimide and 50 ml of dimethylformamide, and the resulting mixture was stirred for 30 minutes. 2.0 g of 6-methylergolin-8β-ylmethyl tosylate was added to the mixture which was then heated on a water bath for 30 minutes. The solvent was distilled off under reduced pressure, and water was added to the residue. The precipitated crystals were separated by filtration, and washed with water. The crystals thus obtained were treated with charcoal in ethanol and recrystallized from ethanol to obtain 0.9 g of the titled compound as colorless needles having a melting point of 233°–238° C. (with decomposition).

NMR (CDCl$_3$) δ: 1.19 (1H, q, J=11.2 Hz), 1.82–3.10 (7H, m), 2.43 (3H, s), 2.72 (4H, s), 3.21–3.74 (3H, m), 6.70–7.20 (4H, m), 7.89 (1H, br).

Elementary Analysis for $C_{20}H_{23}N_3O_2$: Calc'd: C, 71.19; H, 6.87; N, 12.45. Found: C, 71.30; H, 6.95; N, 12.49.

EXAMPLE 9

2-Methyl-1-(6-methylergolin-8β-ylmethyl)imidazole 0.8 g of 50% sodium hydride in an oil was added in small portions to a mixture of 1.2 g of 2-methylimidazole and 16 ml of dimethylformamide, and the resulting mixture was stirred for 30 minutes. 2.0 g of 6-methylergolin-8β-ylmethyl tosylate was added to the mixture which was then heated on a water bath for 3 hours. After allowing the mixture to cool, ice-water was added to the reaction mixture, and the precipitated crystals were separated by filtration, washed with water and purified by silica gel column chromatography (eluted with chloroform). The product was recrystallized from ethanol to obtain 1.1 g of the titled compound as colorless needles having a melting point higher than 300° C. (with decomposition).

NMR (CDCl$_3$) δ: 1.18 (1H, q, J=12.0 Hz), 1.79–3.10 (7H, m), 2.41 (3H, s), 2.43 (3H, s), 3.37 (1H, dd, J=14.2, 4.2 Hz), 3.77 (2H, d, J=6.9 Hz), 6.74–6.93 (4H, m), 7.89 (1H, br).

Elementary Analysis for C$_{20}$H$_{24}$N$_4$: Calc'd: C, 74.97; H, 7.55; N, 17.48. Found: C, 74.71; H, 7.85; N, 17.18.

EXAMPLE 10

2-Ethyl-1-(6-methylergolin-8β-ylmethyl)imidazole 0.9 g of 50% sodium hydride in an oil was added in small portions to a mixture of 3.0 g of 2-ethylimidazole and 60 ml of dimethylformamide, and the resulting mixture was stirred for 30 minutes. 3.0 g of 6-methylergolin-8β-ylmethyl tosylate was added to the mixture which was then heated on a water bath for 1.5 hours. The solvent was distilled off under reduced pressure, and the residue was purified by silica gel column chromatography (eluted with acetone). The product was recrystallized from methanol:isopropyl alcohol to obtain 1.5 g of the titled compound having a melting point of 232°–237° C.

NMR (CDCl$_3$) δ: 1.18 (1H, q, J=12.0 Hz), 1.38 (3H, t, J=7.4 Hz), 1.70–3.10 (7H, m), 2.43 (3H, s), 2.71 (2H, q, J=7.4 Hz), 3.37 (1H, dd, J=14.4, 3.9 Hz), 3.78 (2H, d, J=6.9 Hz), 6.70–7.23 (6H, m), 8.30 (1H, br).

Elementary Analysis for C$_{21}$H$_{26}$N$_4$: Calc'd: C, 75.41; H, 7.84; N, 16.75. Found: C, 75.01; H, 7.86; N, 16.84.

EXAMPLE 11

2-Isopropyl-1-(6-methylergolin-8β-ylmethyl)imidazole 0.9 g of 50% sodium hydride in an oil was added to a mixture of 4.0 g of 2-isopropylimidazole and 40 ml of dimethylformamide, and the mixture was stirred for 30 minutes. 2.0 g of 6-methylergolin-8β-ylmethyl tosylate was added to the mixture which was then heated on a water bath for 2 hours. The solvent was distilled off under reduced pressure, and water was added to the residue. The precipitated crystals were filtered, washed with water and purified by silica gel column chromatography (eluted with acetone). The crystals thus obtained were dissolved in methanol, and isopropyl alcohol was added thereto. The mixture was concentrated and allowed to cool to obtain 0.6 g of the titled compound as colorless needles having a melting point of 283°–288° C. (with decomposition).

NMR (CDCl$_3$) δ: 1.18 (1H, q, J=11.7 Hz), 1.34 (3H, d, J=6.7 Hz), 1.35 (3H, d, J=6.7 Hz), 1.80–3.09 (7H, m), 2.43 (3H, s), 3.37 (1H, dd, J=14.3, 4.4 Hz), 3.80 (2H, d, J=6.8 Hz), 6.65–7.25 (6H, m).

Elementary Analysis for C$_{22}$H$_{28}$N$_4$: Calc'd: C. 75.82; H, 8.10; N, 16.03. Found: C, 76.15; H, 8.39; N, 16.25.

EXAMPLE 12

1-(6-Methylergolin-8β-ylmethyl)-2-propylimidazole 0.68 g of 50% sodium hydride in an oil was added in small portions to a mixture of 2.1 g of 2-propylimidazole and 50 ml of dimethylformamide, and the resulting mixture was stirred for 30 minutes. 2.0 g of 6-methylergolin-8β-ylmethyl tosylate was added to the mixture which was then heated on a water bath for 2.5 hours. The solvent was distilled off under reduced pressure, and the residue was purified by alumina column chromatography (eluted with ethyl acetate:benzene=1:2, and then with ethyl acetate). The resulting product was recrystallized from acetone-hexane to obtain 0.8 g of the titled compound as colorless needles having a melting point of 223°–227° C. (with decomposition).

NMR (CDCl$_3$) δ: 1.01 (3H, t, J=6.9 Hz), 1.17 (1H, q, J=12.0 Hz), 1.60–3.12 (11H, m), 2.43 (3H, s), 3.37 (1H, dd, J=14.4, 3.8 Hz), 3.78 (2H, d, J=6.8 Hz), 6.71–7.25 (6H, m), 7.94 (1H, br).

EXAMPLE 13

1-(6-Methylergolin-8β-ylmethyl)-2-phenylimidazole 1.0 g of 50% sodium hydride in an oil was added in small portions to a mixture of 10.5 g of 2-phenylimidazole and 60 ml of dimethylformamide, and the resulting mixture was stirred for 30 minutes. 3.5 g of 6-methylergolin-8β-ylmethyl tosylate was added to the mixture which was then heated on a water bath for 2 hours. The solvent was distilled off under reduced pressure, and the residue was purified by silica gel column chromatography (eluted with acetone). The product thus obtained was treated with charcoal in dichloromethane, and recrystallized from dichloromethane:isopropyl acetate to obtain 1.0 g of the titled compound as colorless prisms having a melting point of 193°–195° C.

NMR (CDCl$_3$) δ: 1.03 (1H, q, J=12.0 Hz), 1.58–3.04 (7H, m), 2.39 (3H, m), 3.34 (1H, dd, J=14.7, 3.9 Hz), 3.97 (2H, d, J=6.6 Hz), 6.62–6.88 1 (2H, m), 6.94–7.24 (4H, m), 7.28–7.67 (5H, m), 8.04 (1H, br).

Elementary Analysis for C$_{25}$H$_{26}$N$_4$: Calc'd: C, 77.10; H, 6.75; N, 14.33. Found: C, 77.10; H, 6.96; N, 14.34.

EXAMPLE 14

2-Ethyl-4-methyl-1-(6-methylergolin-8β-ylmethyl)imidazole 1.6 g of 50% sodium hydride in an oil was added in small portions to a mixture of 9.0 g of 2-ethyl-4-methylimidazole and 70 ml of dimethylformamide, and the resulting mixture was stirred for 30 minutes. 4.1 g of 6-methylergolin-8β-ylmethyl tosylate was added to the mixture which was then heated on a water bath for 2 hours. The solvent was distilled off under reduced pressure, and water was added to the resulting residue. The precipitated crystals were separated by filtration, washed with water and recrystallized from methanol to obtain 1.0 g of the titled compound as colorless needles having a melting point of 172°–174° C.

NMR (CDCl$_3$) δ: 1.14 (1H, q, J=11.7 Hz), 1.33 (3H, t, J=7.3 Hz), 1.76–3.10 (9H, m), 2.20 (3H, d, J=1.2 Hz), 2.43 (3H, s), 3.37 (1H, dd, J=14.8, 4.1 Hz), 3.69 (2H, d, J=6.8 Hz), 6.51 (1H, s like), 6.63–7.23 (4H, m), 8.14 (1H, br).

EXAMPLE 15

Ethyl
4-methyl-1-(6-methylergolin-8β-ylmethyl)-5-imidazolecarboxylate and ethyl
5-methyl-1-(6-methylergolin-8β-ylmethyl)-4-imidazolecarboxylate 1.6 g of 50% sodium hydride in an oil was added in small portions to a mixture of 10 g of ethyl 4-methyl-5-imidazolecarboxylate and 70 ml of dimethylformamide, and the resulting mixture was stirred for 30 minutes. 4.1 g of 6-methylergolin-8β-ylmethyl tosylate was added to the mixture which was then heated on a water bath for 2 hours. The solvent was distilled off under reduced pressure, and the residue was subjected to alumina column chromatography eluting with ethyl acetate to obtain ethyl 4-methyl-1-(6-methylergolin-8β-ylmethyl)-5-imidazolecarboxylate from the first fraction. The product was recrystallized from dichloromethane-diethyl ether and was colorless prisms having a melting point of 225°–227° C. Yield, 0.7 g. This compound is hereinafter referred to as Compound 15A.

NMR (CDCl$_3$) δ: 1.13 (1H, q, J=11.7 Hz), 1.38 (3H, t, J=7.1 Hz), 1.76–3.08 (7H, m), 2.41 (3H, s), 2.50 (3H, s), 3.37 (1H, dd, J=14.4, 4.2 Hz), 3.83–4.44 [4H, m, 4.30 (2H, q, J=7.1 Hz)], 6.67–6.92 (2H, m), 6.96–7.23 (2H, m), 7.39 (1H, s), 8.02 (1H, br).

From the subsequent fractions of the above alumina column chromatography, ethyl 5-methyl-1-(6-methylergolin-8β-ylmethyl)-4-imidazolecarboxylate was obtained. The product was recrystallized from ethanol-dichloromethane and was colorless prisms having a melting point of 248°–251° C. Yield, 0.8 g. This compound is hereinafter referred to as Compound 15B.

NMR (CDCl$_3$) δ: 1.15 (1H, q, J=11.5 Hz), 1.40 (3H, t, J=7.0 Hz), 1.76–3.09 (7H, m), 2.41 (3H, s), 2.57 (3H, s), 3.37 (1H, dd, J=14.1, 2.6 Hz), 3.79 (2H, d, J=6.5 Hz), 4.34 (2H, q, J=7.0 Hz), 6.64–6.79 (2H, m), 6.94–7.25 (2H, m), 7.36 (1H, s), 8.11 (1H, br).

EXAMPLE 16

Anti-hypertensive Activity

The anti-hypertensive activity of the compounds was determined by the tail cuff method using unanesthetized spontaneously hypertensive rats weighing 300 to 350 g (21 to 25 week old). In this experiment, the systolic blood pressure was determined by the bloodless method using a hemodynamometer. The heart rate was determined simultaneously using a sphygmometer connected to the pulse output. After rats were placed under condition of 40° C. for 10 minutes, the blood pressure was determined by holding the rats in a holder. The test compounds were suspended in a 0.5 wt% aqueous gum arabic. Hydralazine hydrochloride used as a comparative agent was administered as an aqueous solution thereof. The volume of oral administration was 0.5 ml per 100 g of body weight. The results obtained are shown in Tables 1 and 2 below.

TABLE 1

| Compound (Example No.) | Dose mg/kg | Changes in Systolic Blood Presure (Δ mmHg) | | | | |
|---|---|---|---|---|---|---|
| | | 1 | 2 | 4 | 6 | 24 (hrs)* |
| Control | — | −5 | −1 | −7 | −5 | 1 |
| Example 1 | 10 | −78 | −49 | −48 | −60 | −14 |
| Example 2 | 10 | −64 | −36 | −37 | −52 | −11 |
| Example 3 | 10 | −57 | −66 | −31 | −27 | −4 |
| Example 4 | 10 | −37 | −51 | −58 | −49 | −15 |
| Example 6 | 10 | −64 | −67 | −62 | −65 | −14 |
| Example 8 | 10 | −64 | −77 | −59 | −66 | |
| Example 9 | 10 | −50 | −59 | −60 | −55 | −9 |
| Example 10 | 10 | −69 | −64 | −68 | −66 | |
| Example 11 | 10 | −53 | −56 | −54 | −58 | |
| Example 12 | 10 | −69 | −59 | −63 | −59 | |
| Example 13 | 10 | −52 | −46 | −54 | −48 | |
| Example 15B | 10 | −49 | −49 | −59 | −59 | |
| Dihydroergotoxine Methanesulfonate | 10 | −19 | −20 | −13 | −13 | −16 |
| Hydralazine Hydrochloride | 10 | −47 | −52 | −67 | −41 | −22 |

*Time (hour) after administration of the test compound.

TABLE 2

| Compound (Example No.) | Dose mg/kg | Changes in Heart Rate (Δ/min.) | | | | |
|---|---|---|---|---|---|---|
| | | 1 | 2 | 4 | 6 | 24 (hrs)* |
| Control | — | −10 | −11 | −18 | −9 | −7 |
| Example 1 | 10 | −39 | −56 | −25 | −58 | −44 |
| Example 2 | 10 | −39 | −74 | −58 | −56 | −23 |
| Example 3 | 10 | 26 | 1 | 2 | −4 | 1 |
| Example 4 | 10 | −16 | −38 | −52 | −41 | −7 |
| Example 6 | 10 | −8 | −30 | −33 | −21 | −10 |
| Example 8 | 10 | 6 | 3 | −32 | −40 | |
| Example 9 | 10 | −12 | −27 | −36 | −32 | −3 |
| Example 10 | 10 | 2 | −15 | −6 | −11 | |
| Example 11 | 10 | −37 | −21 | −24 | −46 | |
| Example 12 | 10 | −25 | −7 | −8 | −5 | |
| Example 13 | 10 | −46 | −49 | −49 | −55 | |
| Example 15B | 10 | −4 | 5 | −8 | −11 | |
| Dihydroergotoxine Methanesulfonate | 10 | −21 | −42 | −41 | −25 | −6 |
| Hydralazine Hydrochloride | 10 | 65 | 66 | 75 | 64 | 44 |

*Time (hour) after administration of the test compound.

EXAMPLE 17

Gastric Secretion Inhibitory Activity

Rats weighing 200 to 250 g (8 rats per group) which have been fasting for 24 hours before testing were subjected to abdominal section under ether anesthesia, and the pylorus portion was ligated. Immediately after ligation, the test compound was administered into the duodenum as a suspension in a 5 wt% aqueous gum arabic at a volume of 2 ml/kg. The rats were sacrificed after 6 hours, and the stomach was extracted. The gastric juice was collected to determine the volume thereof, and the acidity of the gastic juice was titrated to a pH 7.0 with a 0.02N aqueous sodium hydroxide solution using a pH meter. The acid secretion amount per 6 hours (μEq/6 h) was calculated by (volume of gastric juice × acidity of gastric juice). The results obtained are shown in Table 3 below.

TABLE 3

| Compound (Example No.) | Dose mg/kg | Volume of Gastric Juice | | pH | Total Acidity (mEq/liter) | Volume of Acid Secreted | |
|---|---|---|---|---|---|---|---|
| | | ml/rat | Inhibition (%) | | | μEq/6 h | Inhibition (%) |
| Control | — | 3.78 ± 0.42 | — | 1.88 ± 0.08 | 74.7 ± 6.3 | 421.5 ± 114.7 | — |
| Example 1 | 10 | 1.70** ± 0.31 | 67.8 | 2.57* ± 0.23 | 62.9 ± 3.8 | 112.8* ± 29.4 | 73.3 |
| Example 2 | 10 | 1.94** ± 0.20 | 63.3 | 2.64* ± 0.24 | 61.4 ± 7.5 | 122.9* ± 25.4 | 70.8 |
| Example 3 | 10 | 2.73* ± 0.32 | 48.4 | 2.07 ± 0.22 | 70.0 ± 5.3 | 198.7 ± 34.3 | 52.9 |
| Cimetidine | 100 | 2.10* ± 0.62 | 60.2 | 3.10* ± 0.45 | 43.5* ± 9.4 | 142.5 ± 60.5 | 66.2 |
| Dihydroergo- | 10 | 3.81 ± 0.62 | 27.8 | 2.09 ± 0.15 | 65.9 ± 3.5 | 257.9 ± 49.0 | 38.8 |

EXAMPLE 18

Anti-ulcer Activity

The test compound was administered orally to Donryu male rats weighing 240 to 300 g (7 rats per group) which have been fasting for 24 hours before testing, and, after 30 minutes, indomethacin was administered orally to the rats at a dose of 25 mg/kg. The rats were then maintained for 7 hours without feeding water and foods and then sacrificed. The stomach was extracted and fixed by infusing 7.5 ml of a 2% formalin solution into the stomach. The stomach was incised along the greater curvature thereof, and length (mm) of each ulcer generated in gastric glands was determined. The total length of the ulcer per rat was expressed in terms of an ulcer index.

In this experiment, the test compound was suspended in a 0.5% aqueous gum arabic and administered at a volume of 5 ml/kg. Indomethacin (manufactured by Sigma Co., Ltd.) was administered as a 0.5 wt% aqueous suspension in sodium carboxymethyl cellulose at a volume of 5 ml/kg. As a control, a 0.5 wt% suspension of aqueous gum arabic was orally administered at a volume of 5 ml/kg. The results obtained are shown in Table 4 below.

TABLE 4

| Compound (Example No.) | Dose (mg/kg) | Ulcer Index (mm) | Inhibition (%) |
|---|---|---|---|
| Control | — | 61.2 ± 6.6 | — |
| Example 2 | 10 | 4.4 ± 2.3*** | 92.7 |
| Cimetidine | 100 | 28.3 ± 8.4** | 53.7 |
| Cetraxate | 100 | 52.1 ± 8.7 | 14.9 |
| Sofalcone* | 100 | 59.2 ± 10.5 | 3.4 |

*Sofalcone: [5-[(3-methyl-2-butenyl)oxy]-2-[3-[4-[(3-methyl-2-butenyl)oxy]phenyl]-1-oxo-2-propenyl]phenoxy]acetic acid
**$p < 0.01$
***$p < 0.001$

EXAMPLE 19

Activity on KCN-induced Anoxia in Mice

The test compound was administered intraperitoneally to ddY male mice (4 week old), and, after 30 minutes, KCN (2.5 mg/kg) was administered intravenously from the tail. The time from KCN administration to death was determined. When the mouse survived longer than 3 minutes after KCN administration, the survival time of this mouse was calculated as 180 seconds. The death was judged by respiratory standstill. The number of mice which survived longer than 3 minutes after KCN administration was counted and referred to as number of survival. The results obtained are shown in Table 5 below.

TABLE 5

| Compound (Example No.) | Dose (mg/kg; i.p) | Survival Time (sec.) | Number of Survived Mice/Total Mice |
|---|---|---|---|
| Control | — | 45.2 ± 2.2 | 0/40 |
| Example 2 | 10 | 144.4 ± 17.6*** | 5/8 |
| Example 3 | 10 | 101.6 ± 17.8** | 2/8 |
| Dihydroergotoxine methanesulfonate | 10 | 124.3 ± 16.5*** | 2/8 |
| Calsium Hopantenate | 500 | 43.8 ± 2.5 | 0/9 |
| Meclofenoxate Hydrochloride | 200 | 47.7 ± 4.4 | 0/6 |

**$p < 0.01$
***$p < 0.001$

EXAMPLE 20

Activity on Reserpine-induced Immobility

Reserpine was administered intraperitoneally to ddY male mice (4 week old) at a dose of 2 mg/kg, and, after 18 to 20 hours, the test compound was administered intraperitoneally to the mice. Thereafter, the ambulation (the number of times of the animal crossed the demarcation line) of the mice was counted for a period of 1 minute at 15, 30, 45 and 60 minutes after the administration of the test compound, respectively, according to the open-field method. The total number of ambulation determined at 4 times in each mouse and compared with that of the control. The results obtained are shown in Table 6 below.

TABLE 6

| Compound (Example No.) | Dose (mg/kg; i.p.) | n | Ambulation |
|---|---|---|---|
| Control | — | 16 | 19.1 ± 8.5 |
| Example 6 | 10 | 6 | 198.8 ± 32.2*** |
| Bromocriptine Methanesulfonate | 10 | 6 | 36.7 ± 12.3 |
| Apomorphine Hydrochloride | 3 | 10 | 71.0 ± 7.0*** |

***$p < 0.001$

EXAMPLE 21

Rotational Activity in Rats with Unilateral 6-Hydroxydopamine Lesion of the Substantia Nigra Rats under pentobarbital sodium anesthesia (50 mg/kg, i.p.) were fixed on an apparatus for fixing brain, and 6-hydroxydopamine (8 μg/4 μl) was injected in the substantia nigra (A:3.0, L:2.6, D:7.8) according to Pellegrino & Cushman's atlas. Seven days after the injection of 6-hydroxydopamine, apomorphine was administered subcutaneously at a dose of 0.25 mg/kg, and the rats showing apparatus rotating movement to one side opposite to the destroyed side were selected. After 7 days, the test compound was administered intraperitoneally and, thereafter, rotating movement of the rats was observed over 1 minute at an interval of 5 minutes during a period of 60 minutes. The results obtained are shown in Table 7 below.

TABLE 7

| Compound (Example No.) | Dose (mg/kg, i.p.) | Number of Rotating Movement over 60 min. |
| --- | --- | --- |
| Example 6 | 10 | 0* |
| Apomorphine Hydrochloride | 0.5 | 147 |

*Increase in spontaneous movement and sniffing occurred markedly and were continued for more than 5 hours.

As is apparent from the data shown above, the compounds represented by the formula (I) of this invention possess excellent pharmacological activities.

For example, as shown in Table 1, the compounds of this invention exhibited a very strong and long lasting hypotensive activity as compared with that of the comparative compound, dihydroergotamine. Further, the comparative compound, hydralazine, exhibited tachycardia in human as one of side-effects and also a marked increase in heart rate as shown in Table 2, whereas the compounds of this invention did not increase the heart rate and, rather, did not affect or reduce it.

The compounds of this invention also exhibited a strong gastric secretion inhibitory activity as shown in Table 3, and the degree of inhibition was more than 10 times that of an anti-ulcer agent, Cimetidine (1-cyano-2-methyl-3-[2-[[(5-methylimidazole-4-yl)methyl]thio]ethyl]guanidine). Dihydroergotoxine did not reveal any significant gastric secretion inhibitory activity. Further, as shown in Table 4, the compounds of this invention exhibited a very strong anti-ulcer activity as compared with the comparative compound, Cimetidine. Cetraxate (p-hydroxyhydrocinnamic acid trans-(4-aminomethyl)-cyclohexane carboxylate) and Sofalcone did not show any significant anti-ulcer activity.

The compounds of this invention exhibited an excellent brain projection activity as shown in Table 5. In particular, the compound of Example 2 exhibited the activity higher that that of dihydroergotoxine methanesulfonate. Calcium hopatenate and meclofenoxate hydrochloride which are known to have brain protection activity did not show any significant activity.

Bromocriptine has been known to have an anti-depressive activity as reported in J. Affect. Disord., Vol. 1, 173 (1979), but the compound of this invention exhibited an excellent anti-depressive activity markedly higher than that of bromocriptine as shown in Table 6 as determined by reserpine-induced immobility, one of the anti-depressant test methods.

Further, as shown in Table 7, the compound of this invention exhibited an excellent dopamine-like activity.

The compounds of the formula (I) according to the present invention possess excellent anti-hypertensive activity, vasodilating activity, anti-ulcer activity, gastric secretion inhibitory activity, brain metabolism improving activity, anti-depressive activity and dopamine-like activity, and therefore, are useful for prevention and treatment of various diseases such as hypertension, a wide variety of vein disorders, peptic ulcer, brain abnormality, depression, Parkinson's disease, high prolactin blood disease, etc.

REFERENCE EXAMPLE 1

6-Methylergolin-8β-ylmethyl [Compound described in J. Biol. Chem., Vol. 108, 595 (1935), Helv. Chim. Acta., Vol. 32, 1947 (1949), Collect. Czech. Chem. Commun., Vol. 33, 577 (1968)]

The above compound was prepared by a modified method of the process described in Collect. Czech. Chem. Commun., Vol. 33, 577 (1968).

10 g of sodium borohydride was added in small portions to a mixture of 10 g of 9,10-dihydrolysergic acid methyl ester, 80 ml of methanol and 40 ml of water, and the resulting mixture was refluxed for 1 hour. The reaction mixture was concentrated under reduced pressure, and ice-water was added thereto. The precipitated crystals were separated by filtration, washed with water and dried to obtain 7.2 g of the titled compound as colorless crystals.

REFERENCE EXAMPLE 2

6-Methylergolin-8β-ylmethyl tosylate [Compound described in Helv. Chem. Acta., Vol. 41, 1984 (1958); Collect. Czech. Chem. Commun., Vol. 33, 577 (1968); etc.]

5.0 g of p-toluenesulfonyl chloride was added in small portions to a mixture of 5.0 g of 6-methylergolin-8β-ylmethanol and 50 ml of pyridine while stirring, and the resulting mixture was stirred for 3 hours. After completion of the reaction, 4 ml of water was added to the mixture which was then stirred for 30 minutes. The mixture was diluted with ice-water, rendered alkaline with potassium carbonate and allowed to stand. The precipitated crystals were separated by filtration, washed with water and dried to obtain 6.9 g of the titled compound as colorless crystals. The crystals thus obtained were recrystallized from dichloromethane-isopropyl acetate to obtain colorless leaflets having a melting point of 195°–199° C. (with decomposition).

NMR (CDCl$_3$) δ: 1.07 (1H, br q, J=11.8 Hz), 1.70–3.16 (7H, m), 2.41 (3H, s), 2.44 (3H, s), 3.33 (1H, dd, J=14.6, 4.1 Hz), 3.78–4.13 (2H, m), 6.63–6.88 (2H, m), 6.96–7.40 [4H, m, 7.33 (2H, AB type d, J=8.2 Hz)], 7.78 (2H, AB type d, J=8.2 Hz), 8.04 (1H, br).

While the invention has been described in detail and with reference to specific embodiments thereof, it will be apparent to one skilled in the art that various changes and modifications can be made therein without departing from the spirit and scope thereof.

What is claimed is:

1. An ergoline compound represented by the formula (I)

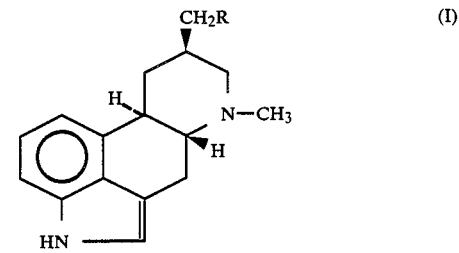

wherein R represents a 5-membered heterocyclic group which contains at least one nitrogen atom as a hereto atom and which is a monovalent group with the nitrogen atom of that group carrying the monovalency, selected from the group consisting of an imidazol-1-yl group, a 2-oxooxazolidin-3-yl group, a 1,2,4-triazol-1-yl group, a tetrazolyl group, a succinimido group, a 2-methylimidazol-1-yl group, a 2-ethylimidazol-1-yl group, a 2-isopropylimidazol-1-yl group, a 2-propylimidazol-1-yl group, a 2-phenylimidazol-1-yl group, a 2-ethyl-4-methylimidazol-1-yl group, a 5- ethoxycarbonyl-4-methylimidazol-1-yl group and a 4-ethoxycarbonyl-5-methylimidazol-1-yl group, and a pharmaceutically acceptable acid addition salt thereof.

2. The ergoline compound 3-(6-methylergolin-8β-ylmethyl)oxazolidin-2-one and a pharmaceutically acceptable acid addition salt thereof.

3. The ergoline compound 1-(6-methylergolin-8β-ylmethyl)-1,2,4-triazole and a pharmaceutically acceptable acid addition salt thereof.

* * * * *